(12) United States Patent
Gaissmaier et al.

(10) Patent No.: US 9,295,751 B2
(45) Date of Patent: *Mar. 29, 2016

(54) USE OF GELATIN AND A CROSS-LINKING AGENT FOR PRODUCING CROSS-LINKING MEDICAL GLUES

(75) Inventors: Christoph Gaissmaier, Kusterdingen-Maehringen (DE); Michael Ahlers, Eberbach (DE)

(73) Assignees: Gelita AG, Eberbach (DE); Tetec Tissue Engineering, Reutlingen (DE)

( * ) Notice: Subject to any disclaimer, the term of this patent is extended or adjusted under 35 U.S.C. 154(b) by 722 days.

This patent is subject to a terminal disclaimer.

(21) Appl. No.: 12/350,320

(22) Filed: Jan. 8, 2009

(65) Prior Publication Data

US 2009/0175946 A1 Jul. 9, 2009

Related U.S. Application Data

(63) Continuation of application No. PCT/EP2007/006105, filed on Jul. 10, 2007.

(30) Foreign Application Priority Data

Jul. 10, 2006 (DE) .......................... 10 2006 033 167

(51) Int. Cl.
| | | |
|---|---|---|
| C09H 7/00 | (2006.01) | |
| A61K 47/42 | (2006.01) | |
| A61L 15/32 | (2006.01) | |
| A61L 24/10 | (2006.01) | |
| A61K 38/00 | (2006.01) | |

(52) U.S. Cl.
CPC .................................. A61L 24/104 (2013.01)

(58) Field of Classification Search
None
See application file for complete search history.

(56) References Cited

U.S. PATENT DOCUMENTS

| | | | |
|---|---|---|---|
| 5,428,014 A | | 6/1995 | Labroo et al. |
| 5,589,322 A | * | 12/1996 | Lobo et al. ..................... 430/449 |
| 5,618,551 A | | 4/1997 | Tardy et al. |
| 5,736,132 A | | 4/1998 | Juergensen et al. |
| 5,834,232 A | | 11/1998 | Bishop et al. |
| 5,936,035 A | | 8/1999 | Rhee et al. |
| 5,939,385 A | | 8/1999 | Labroo et al. |
| 6,007,613 A | | 12/1999 | Izoret |
| 6,039,901 A | * | 3/2000 | Soper et al. ..................... 264/4.3 |
| 6,204,036 B1 | * | 3/2001 | Metzner et al. ............... 435/188 |
| 6,730,299 B1 | | 5/2004 | Tayot et al. |
| 2002/0015724 A1 | | 2/2002 | Yang et al. |
| 2002/0107429 A1 | * | 8/2002 | Wironen ........................ 600/37 |
| 2002/0115090 A1 | * | 8/2002 | Gillis et al. ...................... 435/6 |
| 2003/0095993 A1 | * | 5/2003 | Bentz et al. ................... 424/426 |
| 2004/0036054 A1 | * | 2/2004 | Haslim ........................... 252/70 |
| 2005/0002893 A1 | | 1/2005 | Goldmann |
| 2005/0004663 A1 | * | 1/2005 | Llanos et al. ................ 623/1.46 |
| 2005/0077221 A1 | * | 4/2005 | Berg et al. ................... 210/198.2 |
| 2005/0136104 A1 | * | 6/2005 | Rowe et al. ..................... 424/456 |
| 2005/0232895 A1 | * | 10/2005 | Chen ............................. 424/78.1 |
| 2006/0078962 A1 | * | 4/2006 | Chen et al. .................... 435/68.1 |
| 2007/0077274 A1 | | 4/2007 | Ahlers |
| 2007/0148292 A1 | * | 6/2007 | Royo et al. ..................... 426/103 |

FOREIGN PATENT DOCUMENTS

| | | |
|---|---|---|
| DE | 197 32 917 | 10/1998 |
| DE | 695 17 714 | 11/2000 |
| DE | 694 32 300 | 2/2002 |
| DE | 101 52 407 | 5/2003 |
| DE | 696 30 990 | 12/2004 |
| DE | 600 20 330 | 11/2005 |
| DE | 10 2004 024 635 | 12/2005 |
| EP | 0 856 355 | 8/1998 |
| JP | 2004-283371 | 10/2004 |
| JP | 61-152247 | 7/2006 |
| WO | 94/01508 | 1/1994 |
| WO | 95/09607 | 4/1995 |
| WO | 96/10428 | 4/1996 |
| WO | 96/40304 | 12/1996 |
| WO | 96/40829 | 12/1996 |
| WO | 97/29715 | 8/1997 |
| WO | 97/40137 | 10/1997 |
| WO | 97/40701 | 11/1997 |
| WO | 98/40113 | 9/1998 |
| WO | 99/38543 | 8/1999 |
| WO | 00/12018 | 3/2000 |
| WO | 02/40070 | 5/2002 |

(Continued)

OTHER PUBLICATIONS

Sharecare (2011, updated) "Skin Injury" http://www.sharecare.com/topic/skin-injury, pp. 1-5.*
Leuenberger B. H. L. (1991) Investigation of viscosity and gelation properties of different mammalian and fish gelatins, Food Hydrocolloids, vol. 5, No. 4, pp. 353-361.*
Better Medicine (2011, updated) "Blisters", www.bettermedicine.com/category/ skin-hair-and nails/blisters, pp. 1-5.*
Enk et al. (1999) Mycophenolate is effective in the treatment of pemphigus vulgaris, Arch Dermatol., vol. 135, No. 1, pp. 54-56.*
Cooking Issues (2011, updated), www.cookingissues. com/primers/transglutaminase-aka-meat-glue/, pp. 1-19.*
Chen et al. (2005) Enzyme-catalyzed gel formation of gelatin and chitosan: potential for in situ applications, Biomaterials, vol. 24, pp. 2831-2841.*
Simon-Lukasik et al. (2004) Erythrosin B phosphorescence as a probe of oxygen diffusion in amorphous gelatin films, Food Hydrocolloids, vol. 18, pp. 621-630.*

(Continued)

*Primary Examiner* — Manjunath Rao
*Assistant Examiner* — Samuel Liu
(74) *Attorney, Agent, or Firm* — Leydig, Voit & Mayer, Ltd.

(57) ABSTRACT

The invention relates to the use of gelatin and a cross-linking agent to provide a medical glue which forms a cross-linked gelatin gel in an area of application of the human or animal body. According to the invention, (i) the gelatin and the cross-linking agent are mixed with each other to form the cross-linking medical glue which is then administered to the area of application; or (ii) the gelatin and the cross-linking agent are made available in separate form and are administered, simultaneously or one after the other, to the area of application while forming the cross-linking medical glue.

16 Claims, 6 Drawing Sheets

(56) References Cited

FOREIGN PATENT DOCUMENTS

| | | |
|---|---|---|
| WO | 03/072155 | 9/2003 |
| WO | 2005/020849 | 3/2005 |
| WO | 2005/111121 | 11/2005 |
| WO | 2005/115494 | 12/2005 |
| WO | 2006/059984 | 6/2006 |
| WO | 2006/083384 | 8/2006 |
| WO | 2007/057176 | 5/2007 |
| WO | 2008/006544 | 1/2008 |

OTHER PUBLICATIONS

GMIA (2012) Gelatin Handbook, http://www.gelatin-gmia.com/images/GMIA_Gelatin_Manual_2012.pdf, pp. 1-25.*

Gelatin from porcin skin (2013, updated) http://www.sigmaaldrich.com/catalog/product/sigma/g2500?lang=en&region=US, pp. 1-2.*

"Product Information—Gelatin" (2013, updated) http://www.sigmaaldrich.com/etc/medialib/docs/Sigma/Product_Information_Sheet/g1393pis.Par.0001.File.tmp/g1393pis.pdf, pp. 1-3.*

Chen et al. (2005) 1. Gelatin-based biomimetic tissue adhesive. Potential for retinal reattachment, J. Biomed. Mater. Res. B Appl. Biomater., vol. 77, No. 2, pp. 416-422.*

Yi et al. (2006) influence of transglutaminase-included cross-linking on properties of fish gelatin films, J. Food Sci., vol. 71, pp. E376-E383.*

Vyse Gelatin Company (2014) Gelatin—300 Bloom—Pork-Skin—NF—Superclear™, pp. 1-5.*

Wittich WJ. (A thesis for the degree of mater of engineering (2005) Dept. of Chem. Process Eng., University of Canterburg, New Zealand, pp. 1-81.*

Schrieber, R. et al., "Gelatine Handbook: Theory and Industrial Practice", Wiley-VCH Verlag GmbH & Co. KgaA, Weinheim, ISBN: 978-3-527-31548-2 (2007) Sections 2.3.2.2-2.3.2.5.

"PB Gelatins—Viscosity", PB Leiner PB Gelatins, http://www.pbgelatins.com/about-gelatin/physical-and-chemical-proper printed on Jun. 26, 2012.

Wikipedia, "Poise," http://en.wikipedia.org/wiki/Poise, (Apr. 22, 2014.).

*Technical Dictionary of Abrasive Products*, "Millipoise," FEPA, Paris (2000).

McDermott, Martin K., et al., *Biomacromolecules*, 5(4):1270-1279 (2004).

Chen, Tianhog, et al., *Biomaterials*, 24:2831-2841 (2003).

Ito, Akira, et al., *Journal of Bioscience and Bioengineering*, 95(2):196-199 (2003).

Broderick, Emmett P., et al., *J Biomet Mater Res B Appl Biomater*, 72:37-42 (2004).

Brown, R. Quinn, et al. *J Biomater Res A*, 74:32-38 (2005).

* cited by examiner

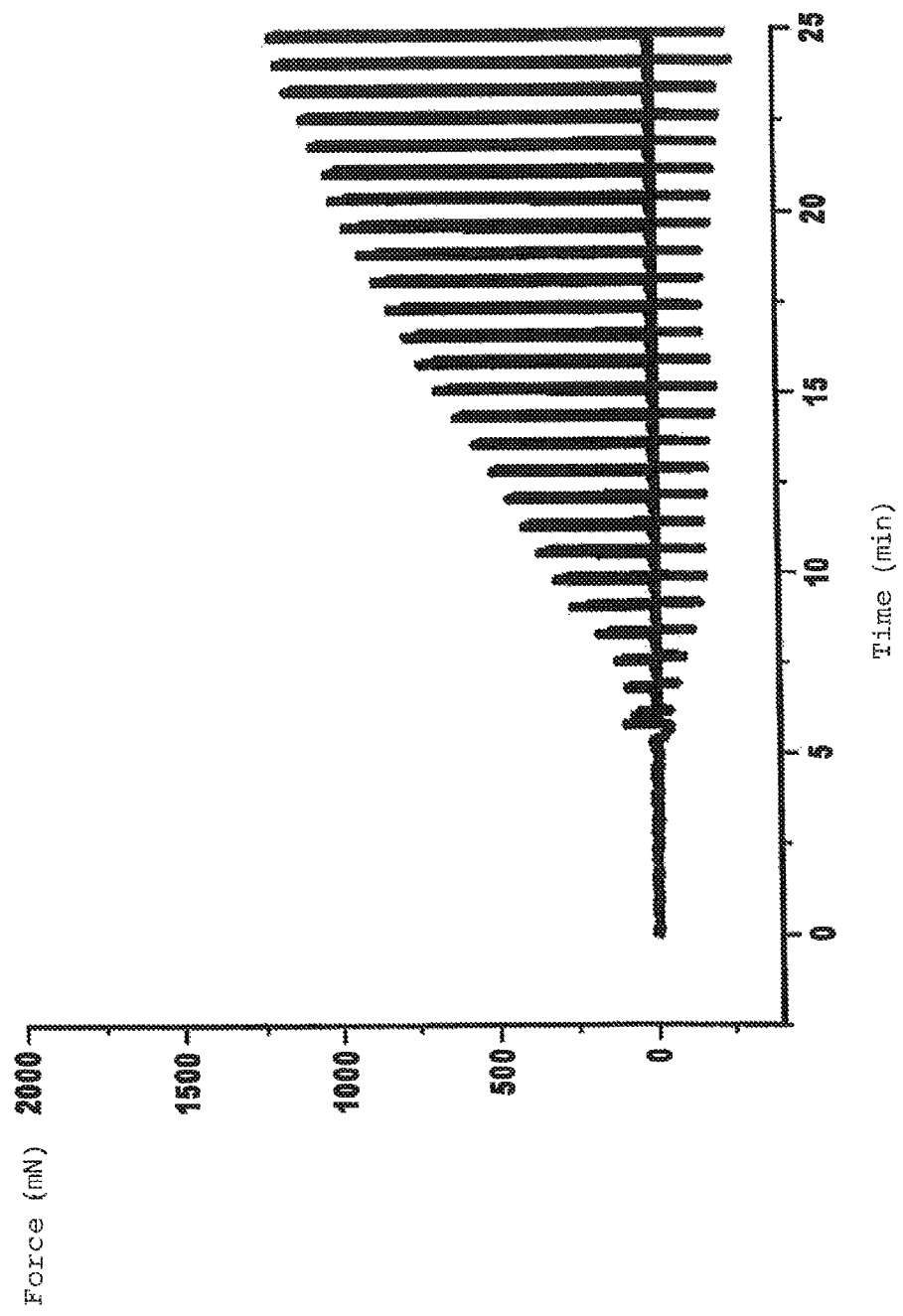

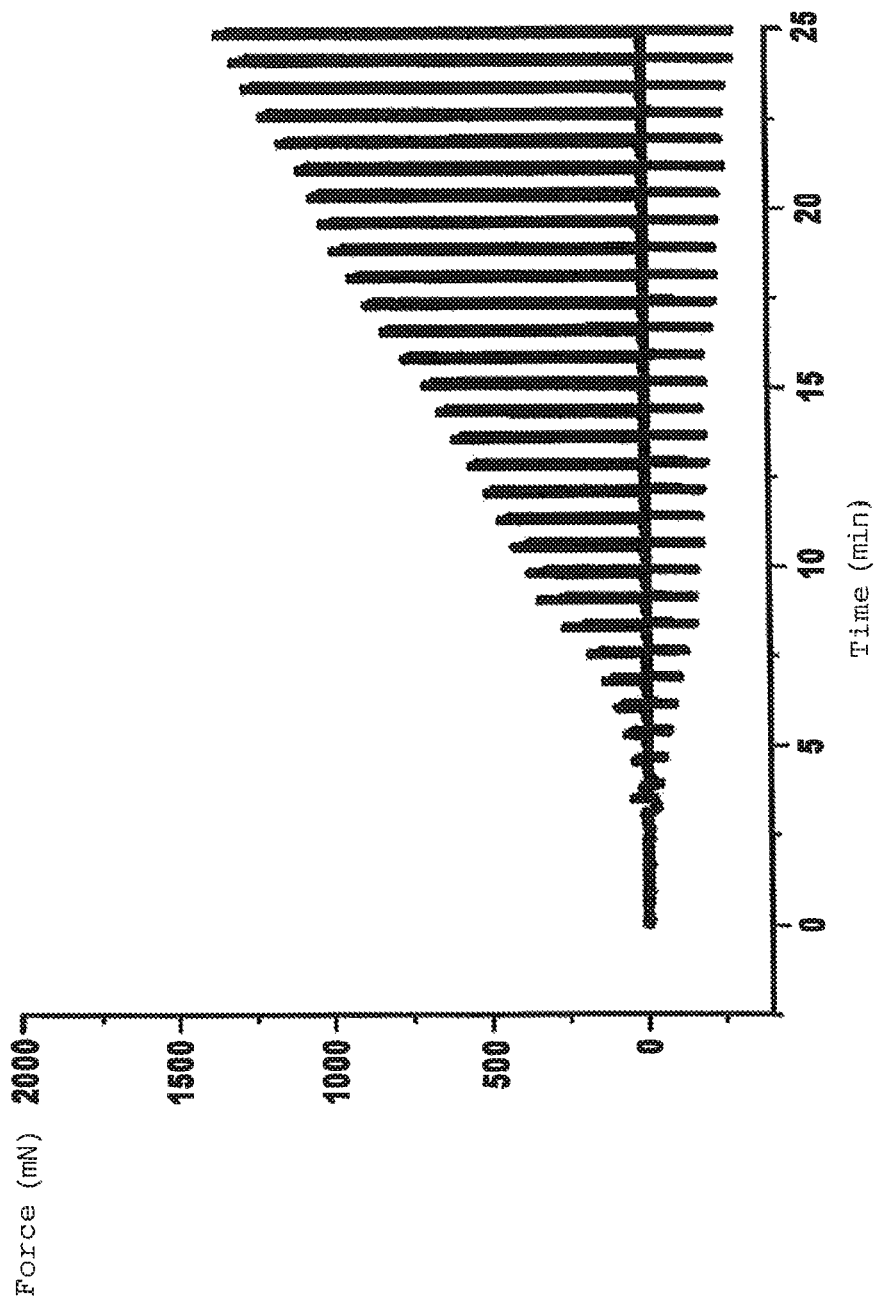

USE OF GELATIN AND A CROSS-LINKING AGENT FOR PRODUCING CROSS-LINKING MEDICAL GLUES

CROSS-REFERENCE TO RELATED APPLICATIONS

This application is a continuation of PCT Application Number PCT/EP2007/006105, filed Jul. 10, 2007, which claims the benefit of German Patent Application Number 10 2006 033 167.2, filed Jul. 10, 2006, which are each incorporated by reference.

BACKGROUND OF THE INVENTION

The invention relates to an innovative use of gelatin and a cross-linking agent for producing a cross-linking medical glue, which forms a cross-linked gelatin gel in an area of application of the human or animal body.

There is a requirement for compositions with adhesive properties, i.e. so-called medical glues, in various areas of medicine. Areas of application of such glues are, for example, fixing tissues, tissue parts or organs in place, also alternatively and/or additionally to surgical suturing, as well as covering or closing wound surfaces or stopping haemorrhaging both internally and externally.

Biodegradable materials, which are degraded after a specific time when the adhesive function is no longer required and resorbed by the body, are primarily suitable as basis for such compositions, which are used in or on the body.

Medical glues are known in practice that comprise different components of human origin and are based on the principle of natural blood coagulation. The main components of such systems are generally thrombin, fibrinogen and blood clotting factor XIII, wherein a solidified gel is formed directly after these components are mixed, i.e. within few seconds. However, in various respects, in particular regarding the kinetics of the gel formation and the viscosity, this gel does not have the desired properties for most applications.

Moreover, when using components of human origin there is a certain risk with respect to the transmission of infectious diseases. Thus, this problem is also posed in the case of the glue composition described in the patent document WO 94/01508 A1, in which a plasma protein or a globular protein is cross-linked with a di- or polyfunctional aldehyde.

Glue systems based on the cross-linkage of bovine serum albumin with glutaraldehyde are also known. However, the use of glutaraldehyde as cross-linking agent poses some problems because of cytotoxic effects.

Document DE 101 52 407 A1 discloses a composition of at least two components, which can be chemically cross-linked with one another for gluing biological tissue, comprising a solution of an amino group-carrying polymer and a solution of an aldehyde with at least three aldehyde groups. Polymers of natural origin such as e.g. deacetylated chitin as well as synthetic polymers are specified as possible amino group-carrying components in this case.

BRIEF SUMMARY OF THE INVENTION

The object of the present invention is to propose a medical glue with improved properties.

To achieve this object, the use of gelatin and a cross-linking agent is proposed according to the invention for producing a cross-linking medical glue of the aforementioned type which forms a cross-linked gelatin gel in the area of application, wherein i. the gelatin and the cross-linking agent are mixed with one another to form the cross-linking medical glue, which is then administered to the area of application; or ii. the gelatin and the cross-linking agent are provided in separate form and are administered simultaneously or consecutively to the area of application with the formation of the cross-linking medical glue.

DETAILED DESCRIPTION OF THE INVENTION

As the main component, the medical glue according to the present invention comprises gelatin as a biocompatible, biodegradable material. The basic principle of the invention is to administer the gelatin in substantially uncross-linked, dissolved form and only change it into a cross-linked gelatin gel, which acts as a medical glue, through the action of a cross-linking agent in the area of application.

A particular advantage of the medical glue according to the invention is that this is cross-linkable in controlled manner. Within the framework of the invention controlled cross-linking ability is to be understood to mean that the maximum strength of the cross-linked gelatin gel is not achieved directly (i.e. within a few seconds) after mixing the gelatin and the cross-linking agent, but that the gel formation occurs in a delayed manner and the gel strength increases continuously within a specific period of time. The kinetics and extent of gel formation can be influenced or controlled in this case by means of different parameters, which are described in detail below.

Besides the gelatin and the cross-linking agent, the medical glue according to the invention does not need any further components that contribute to the formation of the cross-linked gelatin gel. It can thus be synthesised substantially more simply than the above-described system based on thrombin and fibrinogen, which necessarily comprises a plurality of further components. While the function of the present medical glue can be achieved by means of two components, i.e. gelatin and a cross-linking agent, this does not exclude the presence of other constituents. Further advantageous effects can be obtained in some instances by such additional components, as will be described in more detail below.

A further advantage of the invention is that the medical glue does not have to comprise any components of human origin, which makes production simpler and less expensive.

The above-described controlled cross-linkage has the advantage that after mixing the gelatin and the cross-linking agent the treating doctor has sufficient time to apply the medical glue to the area of application, inject it therein or administer it in some other manner. This is important particularly in the case of poorly accessible areas of application, e.g. during the course of operations, since administration is often difficult here and is somewhat time-consuming. Even after the start of the cross-linkage reaction, the medical glue is still plastically deformable for a certain period and can be adapted to the structure of the area of application, e.g. to the surface of a tissue or a cavity to be filled. The viscosity of the glue can already be increasing during this period. This is a significant advantage over thrombin-based glues, which cure more or less abruptly after the components are mixed and can then no longer be deformed.

The medical glue according to the present invention has a high viscosity, i.e. not only with respect to structured surfaces such as tissues, for example, but even with respect to smooth plastic surfaces (e.g. polished polymethyl methacrylate). In comparison, compositions based on thrombin and fibrinogen exhibit a significantly lower viscosity and a significantly reduced adhesion with respect to smooth plastic surfaces.

A reason for the favourable and lasting adhesion properties is that the cross-linked gelatin gel according to the present invention largely exhibits no syneresis, i.e. no shrinkage of the gel occurs with the egress of water. The medical glue according to the invention therefore also has a high dimensional stability, which is also of particular advantage when filling cavities.

The cross-linking glue according to the invention can be applied in different areas of medicine, and therefore different methods of administration can be preferred, depending on the area of application.

Before the different variants of provision and administration of the gelatin and the cross-linking agent are described in detail, the particular advantages that result from the selection of gelatin as biomaterial should firstly be outlined.

In contrast to collagen, gelatin is obtainable in a defined and reproducible composition as well as with high purity. In particular, it contains practically no immunogenic telopeptides that could trigger the defence reactions of the body. On this basis, gelatin has an excellent tissue and cell compatibility, which cannot be guaranteed by other resorbable biomaterials such as alginates or chitosan.

While uncross-linked gelatin is soluble at body temperature (37° C.), it can be changed by cross-linking into a gel-like form, i.e. a cross-linked gelatin gel, that is insoluble in these conditions, as already mentioned.

At the same time, the cross-linked gelatin gel is completely resorbable, i.e. after a certain period it is broken down without residue in the body. This is a hydrolytic degradation that can be assisted by autologous enzymes, if appropriate.

It is possible, in principle, to use gelatin of different origins within the framework of the present invention, wherein porcine gelatin is preferred, in particular gelatin from pig skin. This is available in a high quality and is already approved for different medical applications.

Besides this, the use of other gelatin types such as fish gelatin, for example, can also provide particular advantages. In particular, the gelatin obtained from cold water fish is distinguished by a relatively low gel point, i.e. aqueous solutions of (uncross-linked) fish gelatin remain liquid at lower temperatures, for example, than solutions of pig skin gelatin of the same concentration. This fact allows dissolved fish gelatin to be provided at room temperature or even cooled, which simplifies handling compared to a provision at elevated temperatures of up to 37° C.

To further improve the biocompatibility of the medical glue, it is preferred to use a gelatin with a particularly low content of endotoxins. Endotoxins are metabolites or fragments of microorganisms that occur in raw animal material.

The endotoxin content of gelatin is specified in international units per gram (I.U./g) and determined according to the LAL test, the implementation of which is described in the fourth edition of the European Pharmacopoeia (Ph. Eur. 4).

To keep the content of endotoxins as low as possible, it is advantageous to destroy the microorganisms as early as possible during the course of the gelatin production. Moreover, appropriate hygiene standards should be maintained during the production process.

The endotoxin content of gelatin can thus be drastically reduced by specific measures during the production process. These measures primarily include the use of fresh raw materials (e.g. pig skin) avoiding storage times, with careful cleaning of the entire production plant directly before the start of gelatin production and, if necessary, replacing ion exchangers and filter systems in the production plant.

The gelatin used within the framework of the present invention preferably has an endotoxin content of 1200 I.U./g or less, even more preferred 200 I.U./g or less. Optimally, the endotoxin content lies at 50 I.U./g or less, determined in accordance with the LAL test in each case. In comparison hereto, many commercially available gelatins have endotoxin contents of 20,000 I.U./g and more.

As already mentioned, gelatin that is obtained by extraction from collagen-containing raw materials is a water-soluble product that can be brought into solution in particular at the temperatures suitable for administration, i.e. 37° C. or less. This dissolved form is particularly advantageous for administration, since the solution can be applied, for example, to the surface of a tissue to be treated and evenly distributed there. In order to convert the gelatin into a gelatin gel after administration, i.e. in the area of application of the body, a cross-linkage of the gelatin occurs according to the invention.

If a lower temperature, in particular a temperature lying below the gelling temperature of gelatin (approximately 32 to 33° C.), e.g. 30° C., prevails in the area of application, then an accelerated gelation is surprisingly observed, although the cross-linkage activity of the transglutaminase is reduced at these temperatures compared to a temperature of 37° C. This results is attributable to the fact that the gel formation of the gelatin material itself has an influence besides the cross-linkage reaction, and an increased gelation rate results overall.

Temperatures in the area of application that lie far below the gel point of the gelatin material, e.g. 25° C., are generally not recommended, since an inadequate or irregular cross-linkage of the gelatin material can result here.

Different types of cross-linking agents are known that convert gelatin by inter- and/or intramolecular linkages into a gelatin gel that is insoluble at temperatures of 37° C. or less. These linkages between the gelatin molecules can concern both covalent bonds and a complex formation, which is based, for example, on ionic interactions, hydrogen bridges or Van der Waals forces.

Modified celluloses, in particular hydroxypropylmethyl cellulose (HPMC), are preferably used as complexing cross-linking agents that cause the gelatin to form a gel by means of non-covalent interactions.

Chemical cross-linking agents, which react with the gelatin forming covalent bonds, can also be used within the framework of the present invention. These preferably relate to multifunctional aldehydes, isocyanates, halides or imides, in particular formaldehyde. However, when selecting the chemical cross-linking agent it should be ensured that this does not have any cytotoxic effects on the body, as is the case, for example, with glutaraldehyde (see e.g. patent document DE 101 52 407 A1). Both the quantity of cross-linking agent to be used and the respective area of application of the medical glue should be taken into consideration when assessing possible harmful effects.

Therefore, with the basic requirement of physiological compatibility, application of an enzymatic cross-linking agent is preferred in the present invention. The use of transglutaminase is particularly preferred in this case. This enzyme, which occurs in animals, plants and bacteria, catalyses the hydrolysis of the amide bond of glutamine residues and the cross-linkage of the free acyl group resulting therein with other amino groups. Thus, in the case of proteins, in particular gelatin, transglutaminase primarily catalyses a linkage of glutamine residues with the ε-amino groups of lysine residues, i.e. the formation of both inter- and intramolecular covalent bonds. As a natural enzyme, transglutaminase is recognised as physiologically safe so long as it is used in appropriately purified form.

The use of transglutaminases of bacterial origin that are available in high quality and purity is preferred within the framework of the invention. However, human transglutaminase that can be produced in particular by recombinant gene expression can also be used.

The transglutaminase is preferably used in immobilised form on a support material. This allows a more uniform distribution of the enzyme molecules in the glue, so that a higher activity can be obtained with the same quantity of enzyme. Oligosaccharides are preferred support materials for transglutaminase.

According to the invention, the cross-linkage of the gelatin occurs in the area of application of the body, i.e. the gelatin and the cross-linking agent should only come into contact with one another after, during or directly before administration under conditions that allow the cross-linkage reaction to proceed. To ensure that this occurs, different forms of provision and administration of the gelatin and the cross-linking agent are conceivable. The abovementioned fundamental alternatives (i) and (ii) shall be described in more detail below.

According to variant (i) of the invention, the application of the medical glue occurs so that the gelatin and the cross-linking agent are mixed to form a cross-linking medical glue and this is administered to the area of application. Such a glue is preferably an aqueous solution that contains the cross-linking agent and the gelatin in solution.

With this procedure it is ensured that a homogeneous distribution of both components occurs in the solution. Such a solution can also be administered in a simple manner, in particular by simple application or spraying onto the area of application or by injection. However, such a solution should generally only be produced directly before administration in order to prevent the cross-linkage reaction from being too far advanced before reaching the area of application and prevent the viscosity of the solution from being too high, for example, for an injection. However, depending on the type of gelatin and the cross-linking agent, it is also possible that a solution containing the two components can be stored for some time, in particular at low temperatures, without the cross-linkage reaction already proceeding to an extent detrimental to administration.

The aqueous solution is preferably produced by dissolving a solid mixture comprising the gelatin and the cross-linking agent preferably in lyophilised form. This form of provision is suitable in particular if transglutaminase is used as cross-linking agent.

The provision of gelatin and cross-linking agent in this solid form, in which the enzymatic reaction cannot proceed, has the advantage that the mixture has a relatively high storage stability. At the same time, handling is simple for the treating doctor, since he/she only needs to dissolve a single solid mixture in a liquid medium.

Dissolution of the solid mixture should take place directly before administration of the aqueous solution, i.e. in particular less than 10 minutes, preferably less than 5 minutes beforehand, based on the respectively predetermined temperature in the area of application.

Because the gelatin is present in lyophilised form, its solubility is also significantly improved at lower temperatures. This is important because an application of the medical glue should generally not be made above the body temperature of 37° C. The dissolution of the solid mixture therefore preferably takes place at a temperature of 37° C. or less. At these temperatures, in particular at room temperature, lyophilised gelatin is readily soluble, since it is present at least predominantly in amorphous form.

With respect to the rate of formation of the gelatin gel and also its strength, the quantity of cross-linking agent used in relation to the quantity of gelatin is of decisive importance. In the case where transglutaminase is used, 0.6 to 80 units of transglutaminase per gram of gelatin, further preferred 10 to 40 units/g, are contained in the above-described mixture. The kinetics of the gel formation resulting from the selection of this ratio, amongst other factors, will be discussed in detail below.

Therefore, with respect to the first variant (i), the present invention also relates to a solid mixture that comprises gelatin and transglutaminase preferably in lyophilised form.

In the case of the abovementioned variant (ii) of the invention, application of the medical glue occurs so that the gelatin and the cross-linking agent are provided in separate form and are applied simultaneously or consecutively to form the cross-linking medical glue. In this case, the mixing of the two components can occur at different times, as is described below.

A preferred form of provision is that both the gelatin and the cross-linking agent are provided in the form of separate aqueous solutions. These can then be mixed by the treating doctor and administered in the form of a single solution, as has already been described above. In this case, mixing should occur less than 10 minutes, preferably less than 5 minutes, before administration.

However, to more reliably exclude the possibility of the cross-linkage reaction starting too early, it is preferred if the gelatin solution and the cross-linking agent solution come into contact with one another only during or after administration and not before. This can be achieved in particular by a simultaneous application of the two (separate) solutions.

Depending on the type of means used to administer the solutions (e.g. one or more injection cannulas or other applicators), the mixing of the simultaneously applied solutions can occur before, during or after the area of application is reached in this case. However, it is advantageous to conduct the mixing as early as possible, i.e. before the area of application is reached, in order to assure a high homogeneity of the solution arriving at the area of application and thus assure the formation of a uniformly cross-linked gelatin gel.

In a preferred embodiment of the invention, a simultaneous administration of the gelatin solution and the cross-linking agent solution is conducted by injecting both solutions using a multi-chamber applicator, e.g. a dual-chamber syringe. In this case, the gelatin solution and cross-linking agent solution are located in separate chambers of the applicator and are administrated already mixed, for example, by a common injection cannula to the desired area of application. Therefore, mixing of the two solutions occurs during administration, e.g. upon entry in the cannula. To achieve as intensive a mixing as possible, it is preferred if the multi-chamber applicator comprises a mixing element. In particular, this can be a geometric structure (static mixer) in the flow path of the cannula, at which thorough mixing, in particular swirling, of the two solutions occurs.

Hence, with respect to the second variant (ii), the present invention also relates to a multi-chamber applicator, which contains an aqueous gelatin solution and an aqueous cross-linking agent solution in separate chambers.

Alternatively, it is also possible to administer the aqueous gelatin solution and the aqueous cross-linking agent solution to the area of application one after the other. It is also assured in this case that the cross-linkage of the gelatin only takes place in the area of application.

In a further preferred embodiment of the invention, an aqueous gelatin solution is provided as well as a cross-linking agent in solid form. This variant is particularly suitable in the case of enzymatic cross-linking agents such as transglutaminase, the keeping quality of which is generally higher in this form than in solution. The enzyme can be provided in particular in the form of a lyophilised powder, which is then added in metered dosages to the gelatin solution before administration and then dissolved.

Because of the reasons already mentioned above, it is preferred if the administration of the aqueous gelatin solution occurs at a temperature of 37° C. or less. However, the production of the gelatin solution can also take place at higher temperatures, e.g. at 60° C.

If the solution is then stored at room temperature or with cooling, the gelatin can indeed gelate and solidify, but can then be brought back into solution again directly before administration by heating to 37° C.

The concentration of the administered gelatin solution is preferably selected so that the gelatin concentration in the medical glue amounts to 5 to 20% by wt. It has been found that lower gelatin concentrations generally do not result in gelatin gels with an adequate strength that are readily cross-linked.

In the case where transglutaminase is used as cross-linking agent, the quantity and concentration thereof in a transglutaminase solution is preferably selected so that, as has already been described in association with variant (i), a quantity of 0.6 to 80 units of transglutaminase per gram of gelatin results in the medical glue. A ratio of 10 to 40 units/g is further preferred. In this case, the volume of transglutaminase solution selected can generally be significantly lower than that of the gelatin solution, so that the latter is not significantly diluted by mixing with the transglutaminase solution.

The speed of the cross-linkage reaction as well as the strength of the gelatin gel formed are largely dependent on the gelatin concentration in the medical glue and on the ratio between gelatin and cross-linking agent. These parameters can be varied within the abovementioned preferred ranges to balance the effect of further factors.

Such factors are, for example, the type of gelatin used, in particular its viscosity and average molecular weight, and also the type of cross-linking agent, in particular its type and origin in the case of transglutaminase.

The kinetics and extent of the cross-linkage reaction can be described by means of different physical parameters. To measure these, the formation of the gelatin gel as it proceeds in vivo in the case of a therapeutic application is pursued by a corresponding reaction in vitro. In this case, the start of the cross-linkage reaction is respectively defined by the time at which the gelatin and the cross-linking agent come into contact with one another in the aqueous solution.

The rate of formation of the cross-linked gelatin gel can be characterised in particular by specification of the so-called gel point. In this case, the gel point is defined as the point in time after the start of the cross-linkage reaction at which the storage modulus G' and the loss modulus G" of the gelatin gel are equal in size (see also T. Metzger, Das Rheologie-Handbuch [The manual of rheology], Verlag Vincentz, 2000, pages 173 et seq.).

In an uncross-linked liquid gelatin solution, G' lies clearly below G". During the course of the cross-linkage reaction, i.e. with increasing gelation, both the storage and the loss modulus increase, wherein G' increases more strongly than G". The abovementioned gel point can therefore be determined from the intersection of the two curves in a graph, in which G' and G" are plotted in relation to time. The gel point can also be determined experimentally as the time at which a gel strength (see below) can be measured for the first time during the course of the cross-linkage reaction.

For the use according to the present invention, it is preferred if the gel point of the cross-linked gelatin gel is reached 10 minutes or less after the start of the cross-linkage reaction, particularly preferred 5 minutes or less after the start of the cross-linkage reaction. The abovementioned times respectively relate to the predetermined temperature of the area of application. The gel point can be influenced by the selection of the parameters specified above, depending on the area of application of the medical glue.

As has already been mentioned, the cross-linkage of the gelatin occurs in a controlled manner, i.e. the gel strength increases continuously and only reaches its maximum value a certain time after the gel point. After reaching gel point the medical glue is also still partially plastically deformable and can be adapted to the structure of the area of application. In many cases, a very rapid gel formation is desired, e.g. if haemorrhaging must be stopped during operations by gluing blood vessels. However, if the gel formation occurs too quickly, there is the risk that the medical glue will lose its flowability too early and the treating doctor will not have sufficient time for the application.

With respect to the mechanical properties of the cross-linked gelatin gel, it is preferred if this has a gel strength of 100 g or more, measured with a plunger with a diameter of 12.7 mm at a penetration depth of 4 mm. These details relate to pressing a circular plunger with a diameter of 12.7 mm into the gelatin gel perpendicularly to its surface, wherein the plunger is made of polymethyl methacrylate and has a polished surface (see "Standardised Methods for the Testing of Edible Gelatine", Gelatine Monograph, June 2005, GME).

The gel strength can also be expressed as a force: in the case of a gel strength of 100 g, 0.981 N is necessary to press the plunger into the gelatin gel to a depth of 4 mm. In this case, the gel strength amounts to 774 mN/cm$^2$ relative to the plunger area.

The described gel strength relates to the maximum value reached in the case of the cross-linked gelatin gel. However, the increase in gel strength per unit time, which can also be influenced by the choice of gelatin concentration, the quantity of cross-linking agent etc., is also an important parameter in this context. The increase in gel strength of the cross-linked gelatin gel in the first 10 min after reaching the gel point preferably lies in the range of 5 to 200 mN/cm$^2$·min, in particular 30 to 150 mN/cm$^2$·min.

The adhesion to a smooth plastic surface, e.g. made of polished polymethyl methacrylate, can be applied as dimension for the viscidity of the cross-linked gelatin gel, and this preferably amounts to 200 mN/cm$^2$ or more.

It has already been mentioned that the viscosity of the gelatin used also has an influence on the gel formation besides other factors, wherein a higher viscosity is generally associated with a quicker gel formation. In this context, the viscosity of gelatin is understood to be the viscosity of a 6.7% by wt. standard solution of gelatin in water at 60° C. This preferably amounts to 7 mPa·s or more for the gelatin used within the framework of the present invention.

The viscosity of gelatin is dependent on its origin as well as on the respective production process, and can be further influenced by specific measures.

In a preferred embodiment of the invention, a gelatin is used that has previously undergone a thermal pretreatment at reduced pressure. As a result of such a pretreatment the viscosity of the gelatin can be increased, wherein this effect is primarily attributable to a thermal elimination of water within the gelatin molecules.

The thermal pretreatment is preferably conducted at temperatures of 80 to 160° C., since below 80° C. the observed effects are relatively little pronounced and above 160° C. an undesirable coloration of the gelatin can occur. Values in the range of 90 to 120° C. are most preferred.

The gel formation is additionally dependent on the molecular weight of the gelatin. The use of gelatin with a high average molecular weight, in particular of 140 kDa or more, is preferred, since in this case an insoluble gelatin gel is already obtained with a lower number of cross-linkage points than in the case of a gelatin with a lower molecular weight.

Alternatively or additionally to a purposeful selection or modification of the gelatin used, the properties of the medical glue according to the invention can also be influenced by mixing together two or more gelatins with different viscosities and/or Bloom values. For example, the rate of gel formation can be varied over a broad range as a result of different mixture ratios of high-viscosity bone gelatin with a low-viscosity fish gelatin.

In certain applications it can be required that the medical glue or the solution containing the gelatin already has a relatively high viscosity before the start of the cross-linkage reaction. This is the case, for example, when a pressure is exerted onto the medical glue in the area of application, so that a solution with too low a viscosity would be immediately pressed out of the area of application again.

An increase in viscosity can be advantageously achieved if the medical glue comprises a viscosity-increasing polymer. A preferred viscosity-increasing polymer is, for example, carboxymethylcellulose. By adding this, the viscosity of a gelatin solution can be increased 20-fold and more.

In a further preferred embodiment of the invention, a partially cross-linked gelatin is used for the production of the medical glue, i.e. the gelatin has already undergone a first (partial) cross-linkage step before the administration according to the invention. As described above, the partially cross-linked gelatin can be administered in mixture with the cross-linking agent or simultaneously or consecutively with this, wherein the formation of the cross-linked gelatin gel in the area of application then constitutes a second cross-linkage step.

By using partially cross-linked gelatin, the viscosity of the gelatin solution to be administered can be significantly increased, which is associated with the abovementioned advantages. Moreover, a substantially quicker gel formation can also be achieved by this measure, wherein gel points can be achieved in significantly less than 5 minutes, in particular in the range of a few seconds. A very quick gel formation that occurs almost directly after application of the medical glue can be advantageous in certain applications, if any undesirable discharge of the glue out of the area of application is to be prevented. However, when using partially cross-linked gelatin the advantage of the controlled cross-linkage in the area of application is maintained, i.e. even if the gel formation occurs very quickly, the gel strength subsequently increases continuously and only reaches its maximum value a certain period after gel point.

To ensure that the solution of the partially cross-linked gelatin is highly viscous, but still remains flowable in the conditions of application, the degree of the partial cross-linkage should not be too high. This can be controlled by the conditions in which the partially cross-linked gelatin is produced, in particular by the gelatin concentration, the quantity of cross-linking agent and the duration of the partial cross-linkage reaction. The gelatin used is preferably partially cross-linked by using transglutaminase. Besides the advantages already mentioned above, the use of transglutaminase provides the possibility of stopping the partial cross-linkage reaction by deactivating the enzyme after a defined reaction time, in particular by a thermal denaturing or an oxidising agent such as hydrogen peroxide, for example.

If the partial cross-linkage of the gelatin is achieved by means of transglutaminase, then significantly lower quantities of transglutaminase in relation to the gelatin can be used for this than is the case with the administration of the cross-linking medical glue. The gelatin is preferably partially cross-linked using less than 10 units of transglutaminase per gram of gelatin, in particular using 1 to 3 units of transglutaminase per gram of gelatin.

In some applications it can be advantageous if the medical glue comprises one or more therapeutic active substances, e.g. anti-inflammatory and/or analgesic agents, antibiotic substances and also factors promoting wound healing and/or angiogenesis.

To enable a delayed and/or continuous release, it is preferred if the active substance or substances are present in encapsulated form in the medical glue. In particular, active substances can be encapsulated in gelatin pellets.

In a further advantageous embodiment of the medical glue, this comprises a dye. As a result, during application the treating doctor can recognise precisely at which location the glue is located within the area of application and how much glue has already been applied. Methylene blue, which is biocompatible and clearly contrasts with the tissue, can be used as dye, for example.

Some preferred areas of application of the medical glue according to the invention shall be outlined below.

A preferred embodiment of the invention relates to the use of gelatin and a cross-linking agent for producing a cross-linking medical glue to stop haemorrhaging, wherein the medical glue is applied to an area of application affected by haemorrhaging, so that the haemorrhaging is stopped by the formation of the cross-linked gelatin gel.

According to one of the variants described above, the application to the area of application can occur, in that an aqueous solution containing the gelatin and the cross-linking agent is preferably poured or sprayed thereon. The solution can be evenly distributed and completely cover the affected area. The forming cross-linked gelatin gel forms a protective layer to the outside. In this case, damaged or severed blood vessels located in the area of application are closed or glued by the gelatin gel.

In particular, the invention relates to such applications during operations. The use of the medical glue according to the invention provides particular advantages if surgical interventions are to be conducted on tissues or organs with a particularly heavy blood supply such as the liver or bone, for example. In this case, when applying conventional methods, a plurality of blood vessels would have to be clamped by hand, which is very complicated, time-consuming and frequently also impossible in the case of diffuse haemorrhaging over a large area. In contrast, haemorrhaging can be stopped very quickly and easily when applying the medical glue according to the invention by coating and thus gluing the cut surface on the tissue or organ with the cross-linked gelatin gel.

In this context, the invention also relates to a method for stopping haemorrhaging in humans and in animals, in particular during operations, wherein the method comprises the administration of gelatin and a cross-linking agent separately or already mixed before the area of application is reached.

The invention additionally relates to the use of gelatin and a cross-linking agent for producing a cross-linked medical glue for the treatment of injuries and/or burns of human or animal skin. In the case of such an external application, both an anti-haemorrhagic and a purely protective function of the medical glue are of prime importance. The affected skin areas can be reliably covered as a result of the good adhesion properties.

A further area of application of the invention relates to the use of the medical glue to refix or fix in place autologous tissues (e.g. cartilage or bone fragments) or allogenic tissues (e.g. spongiosa graft of homologous bone) or of different implants in an area of application of the human or animal body. Thus, because of the good adhesive properties of the cross-linked gelatin gel, implants of different types can be fixed in or on the tissue for a specific period of time, i.e. until resorption of the glue.

In addition, resorbable materials can be concerned in the case of implants to be fixed in place. Those materials that have either been colonised beforehand in vitro by living cells or that are populated by cells in vivo after being implanted, should be mentioned in particular here. In these cases, both the biomaterial or support material and the glue undergo a biological degradation.

Synthetic implants that consist at least partially of plastic and/or metal can also be fixed in an area of application using the glue according to the invention. It can be necessary to glue implants in place in such a manner until the surrounding tissue is able to perform an adequate protective function for the implant.

The glue according to the invention can also be used to fix in place and/or close nerve guides. These are tubular implants that serve as guide structures to enable severed nerve pathways to reconnect. Individual nerve cells (axons) respectively grow in the internal space of a nerve guide, wherein their ends must be manually inserted into the tube and fixed in place there. This can be advantageously achieved by gluing the axon in the nerve guide using the medical glue according to the invention. In this application it is particularly advantageous to increase the viscosity of the glue by adding carboxymethyl cellulose, for example, to ensure that in the still uncross-linked state the axon also remains in the tube.

According to a further application of the glue according to the invention, this is used to seal surgical sutures. As a result of the good adhesive properties of the cross-linked gelatin gel, sutures can be effectively sealed in order to prevent undesirable openings between different tissues or organs. In addition, the suture is protected from external stresses.

The glue according to the invention can also be applied for sealing drill channels in bone, e.g. in the case of cruciate ligament replacement. As a result, haemorrhaging is stopped and also the penetration of synovial fluid between the implant and the bone wall is prevented by the seal. According to current findings, the penetration of synovial fluid into the drill channel can result in poor ingrowth of the implant into the bone, which can cause transplant failure at a later stage.

The invention additionally relates to the use of the medical glue as a separation layer for organs or tissue. Such a separating effect of the glue can be desirable or necessary to prevent an undesirable direct contact between different organs and/or tissues, for example, during or after surgical interventions. In this case, the associated tissue can be fixed in place at the same time because of the high adhesive capacity of the glue according to the invention, and therefore it performs a dual function here.

In many applications of the medical glue according to the invention, an additional advantageous effect is provided by the angiogenesis-promoting effect of gelatin. It has been found that in the presence of gelatin, in particular also in cross-linked form, the new formation of blood vessels is stimulated in the tissue. Such an effect is extremely advantageous, for example, in the application of the glue for the treatment of wounds or bone defects, and also in many other cases, since it contributes to the healing and/or regeneration of the affected tissue.

BRIEF DESCRIPTION OF THE SEVERAL VIEWS OF THE DRAWINGS

These and further advantages of the present invention are explained in more detail on the basis of the following examples with reference to the Figures.

FIGS. 1A to 1E: are graphs, in which the gel strength and viscidity of a cross-linked gelatin gel according to the invention are plotted for gelatins with different viscosities in a dependence on the reaction time.

EXAMPLES

Example 1

Figure 1A:
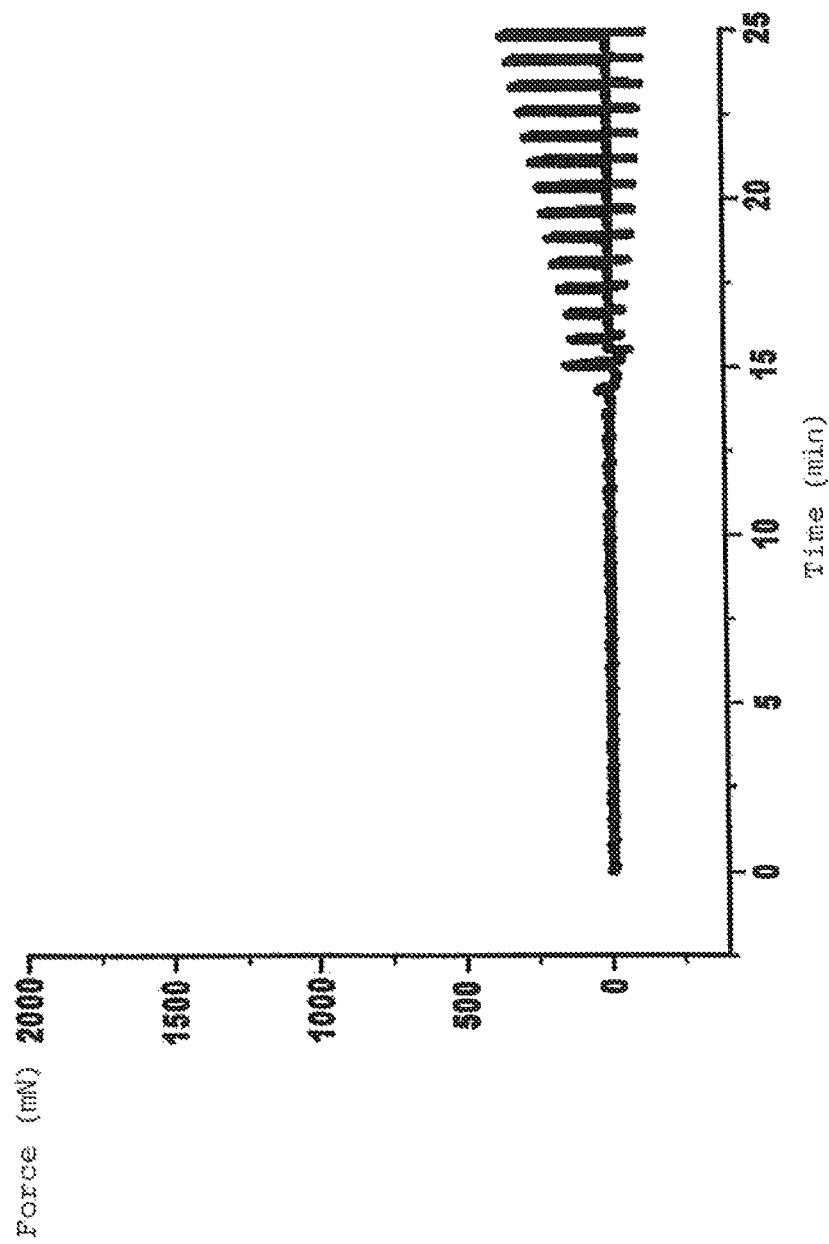
Figure 1C:
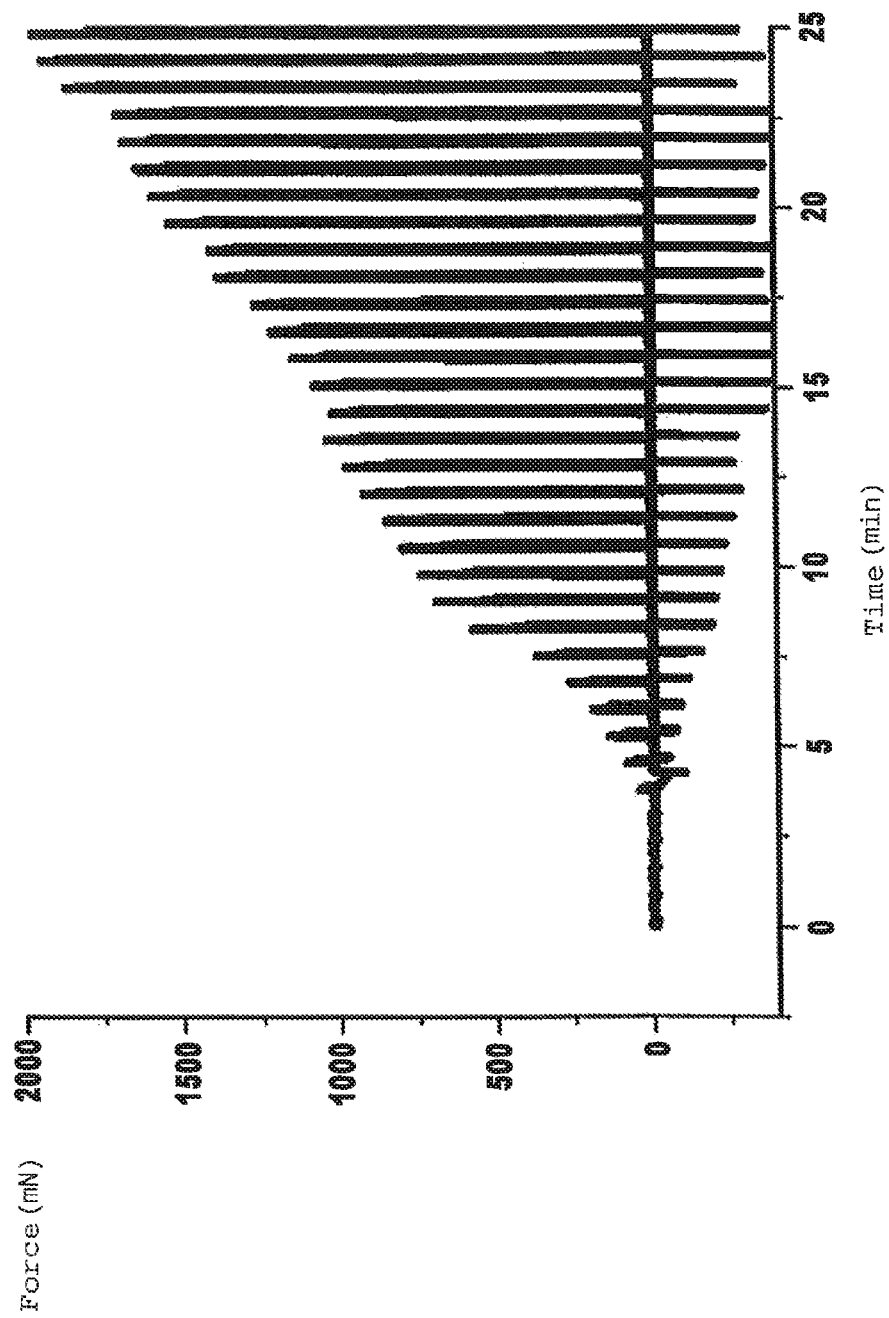

Cross-Linkage of Gelatin with Transglutaminase: Effect of the Viscosity of the Gelatin As a model system for the medical application of the glue according to the invention the cross-linkage of gelatin with the enzymatic cross-linking agent transglutaminase was conducted in vitro and the kinetics of the formation of a cross-linked gelatin gel determined.

Production of a Transglutaminase Stock Solution

A recombinant transglutaminase from human keratinocytes was used for this example and those described below.

A stock solution of transglutaminase with a concentration of 30 units/ml was produced by dissolving the corresponding amount of the enzyme in distilled water at room temperature. The solution was sterilised by filtration, frozen in portions of 1.5 ml each using liquid nitrogen and stored at approximately −18° C.

Thermal Pretreatment of Gelatin at Reduced Pressure

For the cross-linkage with transglutaminase, pig skin gelatins with different viscosities were used in accordance with the following Table 1. The specification of viscosity in this case relates to the viscosity of a 6.7% by wt. aqueous solution of the gelatin at 60° C.

TABLE 1

| Designation | Viscosity (mPa · s) |
| --- | --- |
| Gelatin A | 3.73 |
| Gelatin B | 5.83 |
| Gelatin C | 7.62 |
| Gelatin D | 8.65 |

The high-viscosity gelatins C and D were respectively produced by a thermal pretreatment of gelatins of lower viscosity. In this case, gelatin C was obtained by thermal pretreatment of gelatin B and gelatin D was obtained by thermal pretreatment of a further pig skin gelatin with a viscosity of 6.41 mPa·s.

The thermal pretreatment of the gelatin at reduced pressure was conducted so that approximately 700 g of gelatin in ground form were respectively held under a vacuum of approximately 14 mbar for 4 hours at 105° C. by means of a rotary evaporator. The gelatin was then allowed to cool overnight in a closed vessel.

Execution of the Cross-Linkage Reaction

For each of the four gelatins A, B, C and D, a 10% by wt. solution of gelatin was produced in a mixture comprising 30% by vol. of PBS buffer (pH 7.2) and 70% by vol. of distilled water. For this, the gelatin was dissolved at 60° C. and the temperature of the resulting homogeneous solution was regulated to 37° C.

All the cross-linkage reactions were conducted at a constant temperature of 37° C. in order to approach as far as possible the conditions prevailing in the medical application. For each batch 5 ml of the 10% by wt. gelatin solution were placed in a cylindrical vessel with a diameter of 3 cm, the temperature of which was regulated to 37° C. by means of an aluminium block. The cross-linkage reaction was started by adding 0.3 ml of the transglutaminase stock solution (30 units/ml) and 0.9 ml of distilled water, each preheated to 37° C., and immediately mixing the resulting reaction mixture thoroughly. This corresponds to an enzyme quantity of 18 units/g relative to the gelatin.

Determination of the Gel Strength as a Function of the Reaction Time

During the course of the cross-linkage reaction, the gel strength and the viscidity of the reaction mixture were determined at intervals of 50 sec by means of a force/distance measuring device of the type Zwick BZ 2.5/TN1S (manufacturer: Zwick GmbH & Co. KG, Ulm).

The determination procedure is such that in each measurement cycle, i.e. every 50 sec, a circular plunger with a diameter of 12.7 mm is plunged or pressed 4 mm deep into the surface of the reaction mixture perpendicularly thereto and the force required for this is measured. The plunger, which has a polished polymethyl methacrylate surface, is then pulled upwards again. If a cross-linked gelatin gel is already present, this adheres to the plunger during its removal. The necessary force to pull the plunger so far upwards that the gelatin gel detaches is also measured.

The measured force as a function of the reaction time (start of the cross-linkage reaction at 0 min.) for the four batches with gelatins A, B, C and D is plotted in FIGS. 1A to 1D. The positive force values indicate the force necessary to press the plunger in, i.e. the gel strength (981 mN correspond to a gel strength of 100 g). The negative force values indicate the viscidity (adhesion) of the gelatin gel, i.e. the force required to remove the plunger until the gelatin gel detaches.

During an initial phase of the reaction, both the gel strength and the viscidity lie substantially at zero, i.e. a flowable solution is present. In the medical application, this corresponds to the period, in which the mixture can be administered to the area of application of the body. The earliest time at which a gel strength noticeably different from zero can be measured is the gel point. At this time, the storage modulus G' and the loss modulus G" are the same magnitude.

The different gel points of batches A to D are listed in the following Table 2, wherein the values are respectively averaged from three experiments. The gel strength and adhesion of the gelatin gel relative to surface area, which were measured 10 min after the gel point are respectively specified (the plunger area amounts to 1.267 cm$^2$). These specifications serve primarily to compare the different batches with one another; it is clear from FIGS. 1A to 1D that significantly higher values are obtained in the further course of the cross-linking reaction in particular in the case of the gel strength.

TABLE 2

| Batch | Viscosity of the gelatin | Gel Point | Gel Strength after 10 min | Adhesion after 10 min |
|---|---|---|---|---|
| Gelatin A | 3.73 mPa · s | 14 min | 281 mN/cm$^2$ | 103 mN/cm$^2$ |
| Gelatin B | 5.83 mPa · s | 5 min | 536 mN/cm$^2$ | 167 mN/cm$^2$ |
| Gelatin C | 7.62 mPa · s | 3.3 min | 837 mN/cm$^2$ | 225 mN/cm$^2$ |
| Gelatin D | 8.65 mPa · s | 2.3 min | not measured | not measured |

It is evident that the gel point correlates with the viscosity of the gelatin used, i.e. with the same quantity of cross-linking agent the gel formation occurs substantially more quickly in a high-viscosity gelatin, than in a low-viscosity one.

After reaching the gel point, the gel strength increases continuously and substantially linearly in all four batches. The rate of increase is evident from the gel strength after 10 min specified in Table 2, i.e. it amounts to 28.1 mN/cm$^2$·min for gelatin A. The fact that the maximum gel strength is reached only gradually, is a significant advantage for the application of the medical glue. As a result of the controlled progress of the cross-linkage, the glue can also be distributed after administration, plastically deformed and adapted to the respective tissue structures.

In the case of batches A, B and C the gel strength and adhesion measured after 10 min likewise correlate with the viscosity of the gelatin used, as is also the case for the gel point. In the case of gelatin D, the viscosity of which is slightly higher than that of gelatin C, the gel point is reached very quickly, but the gel strength and adhesion after 10 min are lower.

Example 2

Cross-Linkage of Gelatin with Transglutaminase: Effect of the Gelatin Concentration In this example the thermally pretreated gelatin C from Example 1 was cross-linked with different gelatin concentrations with transglutaminase. The preparation of the reaction mixtures and the measurement of the gel strength were conducted as described in Example 1.

The concentration of the gelatin solutions used, the composition of the reaction mixtures and the gel point resulting from the gel strength measurement are shown in the following Table 3.

The gel strength and adhesion in relation to area 10 min after the gel point are additionally specified.

TABLE 3

| | Batch | | | |
|---|---|---|---|---|
| | 2-1 | 2-2 | 2-3 | 2-4 |
| Concentration of the gelatin solution | 5% by wt. | 8% by wt. | 10% by wt. | 12.7% by wt. |
| Gelatin solution | 5.9 ml | 5.9 ml | 5 ml | 5.9 ml |
| Transglutaminase stock solution | 0.2 ml | 0.3 ml | 0.3 ml | 0.5 ml |

TABLE 3-continued

| | Batch | | | |
|---|---|---|---|---|
| | 2-1 | 2-2 | 2-3 | 2-4 |
| Distilled water | — | — | 0.9 ml | — |
| Transglutaminase per gram of gelatin | 20.3 units/g | 19.1 units/g | 18.0 units/g | 20 units/g |
| Gel point | 5.0 min | 4.0 min | 3.3 min | 2.0 min |
| Gel strength after 10 min | 265 mN/cm$^2$ | 587 mN/cm$^2$ | 837 mN/cm$^2$ | 869 mN/cm$^2$ |
| Adhesion after 10 min | 79 mN/cm$^2$ | 137 mN/cm$^2$ | 225 mN/cm$^2$ | 300 mN/cm$^2$ |

The results show that the gel formation can be accelerated by an increase of the gelatin concentration. The gel point is reached earlier and the gel strength and adhesion achieved after a specific period are higher. This trend is clearly evident in the conducted tests, although in the case of the higher gelatin concentrations the quantity of cross-linking agent was partially lower in relation to the gelatin.

The selection of the gelatin concentration thus provides the possibility of adjusting the medical glue according to the invention to the special requirements of different areas of use. Thus, a relatively rapid gel formation is desired, for example, if haemorrhaging must be stopped during the course of an operation, whereas a slower gel formation can be advantageous when fixing implants in place, since this then enables the doctor to take his/her time to adjust the precise position of the implant after application of the glue.

Example 3

Cross-Linkage of Gelatin with Transglutaminase: Effect of the Quantity of Cross-Linking Agent In this example the thermally pretreated gelatin C from Example 1 was cross-linked with different quantities of transglutaminase.

An 8% by wt. solution of gelatin C was produced as described in Example 1. For each batch 5.9 ml of this solution were preheated to 37° C. and mixed with the quantity of transglutaminase stock solution (30 units/ml heated to 37° C.) specified in the following Table 4 in order to start the cross-linkage reaction. The determination of the gel point by means of the gel strength measurement occurred as described in Example 1.

TABLE 4

| | Batch | | |
|---|---|---|---|
| | 3-1 | 3-2 | 3-3 |
| Quantity of Transglutaminase stock solution | 0.2 ml | 0.3 ml | 0.5 ml |
| Transglutaminase per gram of gelatin | 12.7 units/g | 19.1 units/g | 31.8 units/g |
| Gel point | 6.0 min | 4.0 min | 3.0 min |

As can be seen from the values specified in Table 4, the rate of formation of the cross-linked gelatin gel can also be influenced by the concentration of the cross-linking agent, in this case the transglutaminase. As expected, a higher quantity of cross-linking agent leads to a quicker gel formation.

Example 4

Cross-Linkage of Gelatin with Transglutaminase: Use of Gelatin from Different Raw Material Sources In this example gelatin from cattle bone (bovine limed bone) and also fish gelatin, which does not gelate under the conditions of the standard Bloom test, were cross-linked with transglutaminase with different gelatin concentrations. The preparation of the reaction mixtures and the measurement of the gel strength were conducted as described in Example 1.

The gelatin types, the concentrations of the gelatin solutions used, the composition of the reaction mixtures and the gel points resulting from the gel strength measurement are represented in the following Table 5. The gel strength and adhesion relative to area 10 min after the gel point are additionally specified.

TABLE 5

| | Batch | | | |
|---|---|---|---|---|
| | 4-1 | 4-2 | 4-3 | 4-4 |
| Gelatin type | cattle bone | cattle bone | fish gelatin | fish gelatin |
| Bloom value | 240 g | 240 g | (non-gelating) | (non-gelating) |
| Viscosity (6.7% by wt., 60° C.) | 9.2 mPa·s | 9.2 mPa·s | 2.1 mPa·s | 2.1 mPa·s |
| Concentration of the gelatin solution | 8% by wt. | 8% by wt. | 15% by wt. | 15% by wt. |
| Gelatin solution | 5.9 ml | 5.4 ml | 5.4 ml | 4.8 ml |
| Transglutaminase stock solution | 0.6 ml | 1.0 ml | 1.0 ml | 1.6 ml |
| Transglutaminase per g of gelatin | 38 units/g | 69 units/g | 37 units/g | 67 units/g |
| Gel point | 3.0 min | 1.5 min | 14.5 min | 9.3 min |
| Gel strength after 10 min | 395 mN/cm$^2$ | 870 mN/cm$^2$ | 395 mN/cm$^2$ | 710 mN/cm$^2$ |
| Adhesion after 10 min | 80 mN/cm$^2$ | 95 mN/cm$^2$ | 195 mN/cm$^2$ | 240 mN/cm$^2$ |

The results show that by using low-viscosity fish gelatin, significantly later gel points can be obtained compared to cattle bone gelatin, and this occurs with almost double the gelatin concentration. However, in spite of the later gel formation in the case of fish gelatin, comparable gel strengths are achieved, and the adhesion (viscidity) is even significantly higher (in each case 10 min after gel point). As was to be expected, the increase in the cross-linking agent concentration in both gelatins leads to an earlier gel point and to a higher gel strength (batches 4-2 and 4-4 compared to batches 4-1 and 4-3).

A particular advantage when using non-gelating fish gelatin is that the gelatin solution remains liquid at room temperature and the provision and handling of the medical glue are simplified as a result.

The use of mixtures of different gelatin types, e.g. fish gelatin with cattle bone gelatin or pig skin gelatin, provides further possibilities (besides variation of the gelatin and cross-linking agent concentration) of influencing the gel point, gel strength and adhesion of the medical glue.

Example 5

Cross-Linkage of Gelatin with Transglutaminase: Use of a Gelatin/Carboxymethylcellulose Blend A cross-linkage of gelatin with transglutaminase was also conducted in this example, wherein a gelatin blend was firstly produced to significantly increase the initial viscosity of the uncross-linked gelatin solution. This blend contained 92% by wt. of a pig skin gelatin (261 g Bloom) and 8% by wt. of carboxymethylcellulose (CMC, average substitution rate 0.7; viscosity approximately 8000 mPa·s in 1% by wt. solution at 25° C.). The gelatin/CMC blend had a Bloom value of 260 g and a viscosity of 162 mPa·s (6.7% by wt. at 60° C.).

The preparation of the reaction mixture and the measurement of the gel strength were conducted as described in Example 1, wherein 5.0 ml of an 8% by wt. solution of the blend were firstly produced and mixed with 0.3 ml of transglutaminase stock solution and 0.9 ml of distilled water (this corresponds to 22.5 units of transglutaminase per gram of gelatin/CMC blend).

The gel point in this test was at 4.0 min. 10 min after the gel point a gel strength of 350 mN/cm$^2$ and an adhesion of 70 mN/cm$^2$ were measured.

A comparison with batches 2-2 and 3-2 shows that in spite of the clear increase in the initial viscosity of the gelatin solution by the addition of CMC, the kinetics of the cross-linkage reaction are not influenced significantly by this. This provides an additional possibility of adapting the medical glue to the respective requirements: by means of a gelatin/CMC blend a solution can be provided that is already highly viscous before the cross-linkage, but is still flowable, and this is a great advantage in the closure of nerve guides.

Example 6

Cross-Linkage of Gelatin with Transglutaminase: Use of a Partially Cross-Linked Gelatin In this example the gelatin was firstly subjected to a partial (first) cross-linkage step to increase the initial viscosity of the gel solution and to obtain a significantly quicker gel formation in the actual (in this case second) cross-linkage step.

A gelatin made from pig bones with a Bloom value of 250 g and a viscosity of 6.6 mPa·s (6.7% by wt. at 60° C.) served as starting material for the production of the partially cross-linked gelatin. A 10% by wt. solution of this gelatin in distilled water was prepared by firstly swelling the gelatin for 45 minutes at room temperature and then dissolving it for one hour at 60° C. The temperature of the solution was then regulated to 50° C. and the corresponding quantity of transglutaminase stock solution (30 units/ml) was added, so that a quantity of 1.5 units of transglutaminase per gram of gelatin was present. To conduct the partial cross-linkage the solution was held at 50° C. for 2 hours with agitation.

To stop the cross-linkage reaction, the transglutaminase was thermally deactivated by heating the solution to 80° C., then the solution was cooled immediately in an ice bath, poured into a dish and allowed to gelate. The gelatin gel obtained was minced, dried at 20° C. and at a relative air humidity of 10% and then ground. The partially cross-linked gelatin obtained in this way is referred to below as P2.

A further partially cross-linked gelatin with a slightly higher degree of cross-linkage was produced as described above, except that the partial cross-linkage reaction was conducted for 3 hours. This gelatin is referred to below as P3.

The Bloom values and viscosities at 60° C. and 37° C. of the initial gelatin P0 and the partially cross-linked gelatins P2 and P3 are shown in the following Table 6.

TABLE 6

| | Gelatin | | |
|---|---|---|---|
| | P0 | P2 | P3 |
| Bloom value | 250 g | 228 g | 257 g |
| Viscosity (6.7% by wt., 60° C.) | 6.6 mPa·s | 9.6 mPa·s | 16.7 mPa·s |
| Viscosity (10% by wt., 37° C.) | 28.6 mPa·s | 69.8 mPa·s | 200 mPa·s |

As a result of the partial cross-linkage, the viscosity of the gelatin at 60° C. could be increased approximately 1.5-fold (P2) or approximately 2.5-fold (P3) compared to the uncross-linked gelatin (P0). The effect of the increase in viscosity is even more significant at 37° C., i.e. at a preferred application temperature of the medical glue. Here, the viscosity increased approximately 2.5-fold or approximately 7-fold.

A cross-linkage reaction with transglutaminase was conducted using gelatins P0, P2 and P3 and the gel strength and viscosity were determined as a function of the reaction time, as described in Example 1. In each case, the starting point was 5 ml of a 10% by wt. gelatin solution, to which 1.2 ml of the transglutaminase stock solution (30 units/ml) were added. This corresponds to an enzyme quantity of 72 units per gram of gelatin.

The measurement results are listed in the following Table 7.

TABLE 7

| | Batch | | |
|---|---|---|---|
| | P0 | P2 | P3 |
| Gel point | 1.5 min | 50 sec | <5 sec |
| Gel strength after 10 min | 1184 mN/cm$^2$ | 592 mN/cm$^2$ | 631 mN/cm$^2$ |
| Adhesion after 10 min | 316 mN/cm$^2$ | 197 mN/cm$^2$ | 237 mN/cm$^2$ |

It is evident that the gel point of the cross-linked gelatin gel can be reached substantially more quickly as a result of the partial cross-linkage of the gelatin. Particularly noteworthy is the result achieved with gelatin P3, i.e. an almost immediate gel formation within less than 5 sec after mixing the gelatin with the transglutaminase.

Figure 1E:
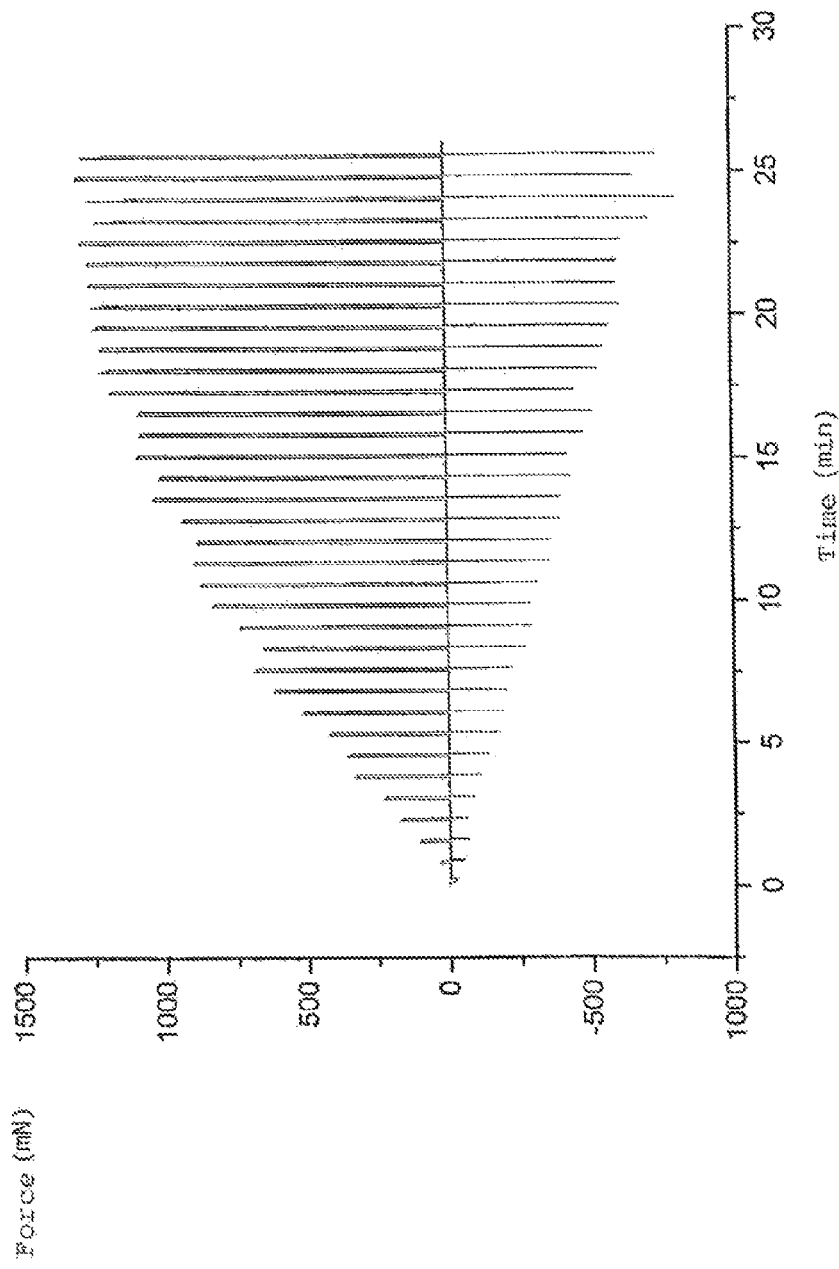

In FIG. 1E the measured force is represented as a function of the reaction time for the batch with gelatin P3 (measurement conducted as described in Example 1). It is clear from the Figure that in spite of the gelation, which occurs almost directly after mixing, the gel strength and the adhesion continuously increase and reach their maximum only some time after gel point. This effect is extremely advantageous for the application of the present invention and as a result the medical glue can be still plastically deformable for a certain period after application and can be adapted to the structure of the area of application.

Example 7

Analysis of the Adhesive Force of the Medical Glue when Gluing Tissue In Vivo

In this example the adhesive action of the medical glue according to the invention was tested on living tissue under clinical conditions. The gelatin C described in Example 1 and transglutaminase as cross-linking agent were used in this case.

A 12% by wt. gelatin solution in PBS buffer was produced as described in Example 1 and fed into the first chamber of a dual-chamber syringe. A corresponding quantity of the transglutaminase stock solution described in Example 1 was fed into the second chamber of the syringe, so that a quantity of 30 units of transglutaminase per gram of gelatin was present.

For the practical test the ventral subcutaneous tissue of an anaesthetised mouse (Blab/c mouse) was lifted off the fascia and a plurality of sections of skin tissue each with an area of approximately 1 $cm^2$ were then prepared. The two components of the medical glue, which had previously been heated to 37° C. in the dual-chamber syringe, were then mixed together and applied simultaneously to the fascia in a quantity of approximately 0.2 ml/$cm^2$. The prepared subcutaneous tissue was inserted to fit precisely and fixed in place by applying light pressure. The bond was then subjected to a mechanical tensile load test. After an adhesion time of approximately 4 minutes after application of the glue a stable bond between the subcutaneous tissue and fascia could be observed on the individual tissue sections.

The test was repeated multiple times with the same result, wherein no other complications arose.

Example 8

Use of the Medical Glue In Vivo as Wound Closure

In order to test whether the medical glue according to the invention is suitable for stopping diffuse haemorrhaging under clinical conditions, an atypical wedge resection on the left liver lobe was conducted on an anaesthetised mouse (Blab/c mouse). Approximately 0.1 ml of the medical glue described in Example 6 were applied to the haemorrhaging cut surface having a length of approximately 0.6 cm using a dual-chamber syringe. A complete stoppage of the haemorrhaging was achieved within 5 minutes after use of the glue.

The test was repeated multiple times with the same result, wherein no other complications arose.

Example 9

Production and Dissolution Behaviour of a Lyophilised Solid Mixture of Gelatin and Transglutaminase This example describes the production of a solid mixture containing 6 units of transglutaminase per gram of gelatin.

75 g of gelatin A from Example 1 (pig skin gelatin with 290 g Bloom) were swelled in 425 g of distilled water and dissolved at 60° C. The solution was allowed to cool to 45° C., mixed with 15 ml of the transglutaminase stock solution (30 U/ml, see Example 1) and thoroughly mixed. Two freeze-drying trays were cooled with liquid nitrogen, the solution containing gelatin and transglutaminase distributed therein and frozen using liquid nitrogen. The frozen solution was lyophilised for two days in a Lyovac GT 2-s freeze-drying installation (manufacturer: AMSCO Finn-Aqua GmbH, Hürth).

The lyophilised solid mixture obtained was ground to a fine powder in a mortar under constant cooling with liquid nitrogen and then dried in a vacuum. Since the powder is highly hygroscopic, it was stored hermetically sealed at approximately 4° C.

A further solid mixture was produced by repeating the described procedure with the same ratios, but by using a cold water-soluble instant gelatin in place of gelatin A. This instant gelatin contains approximately 15% by wt. of low-molecular gelatin hydrolysate to improve its solubility.

The dissolution behaviour of the solid mixtures produced in this way was examined as follows: 50 mg of solid mixture in each case were weighed into a closable tube and mixed with 950 µl of PBS buffer (pH 7.2) preheated to 37° C. The tubes were shaken using a test tube shaker and the time up to visible dissolution of the solid mixture determined.

The mixture produced from gelatin A was dissolved after 2.7 min, the mixture produced from the instant gelatin was dissolved after only 2 min.

The example shows that lyophilised gelatin can be dissolved at 37° C. or less in an aqueous solution. This is attributable to the fact that the gelatin is present largely in amorphous form as a result of the freeze-drying process. The dissolution rate can be improved further by using instant gelatin.

Such lyophilised solid mixtures of gelatin and a cross-linking agent can be advantageously used within the framework of the present invention. The mixture can be provided at room temperature or cooled and can then be dissolved in an aqueous solution at 37° C. or less by the treating doctor.

Comparative Example

Comparison of the Gel Formation in a Composition Based on Thrombin and Fibrinogen For comparison with the present invention, the kinetics of the gel formation were examined in a commercially available medical glue based on thrombin and fibrinogen. This fibrin glue is based on the principle of natural blood coagulation and comprises two components to be mixed having the following composition:

1st component: adhesive protein solution containing:
human plasma protein fraction with fibrinogen
blood clotting factor XIII
plasma fibronectin
aprotinin (bovine)

2nd component: thrombin solution containing:
thrombin (human)
calcium chloride

In order to determine the gel formation kinetics of the fibrin glue, both components were preheated to 37° C. for 20 min and then mixed in a cylindrical vessel (diameter 3 cm), the temperature of which was regulated to 37° C. by means of an aluminium block. The mixing of the components defines the starting time (0 min). The measurement of the gel strength and viscidity (adhesion) of the composition as a function of the reaction time was conducted by means of the force/distance measuring device of the type Zwick BZ 2.5/TN1S as described above.

Figure 2:
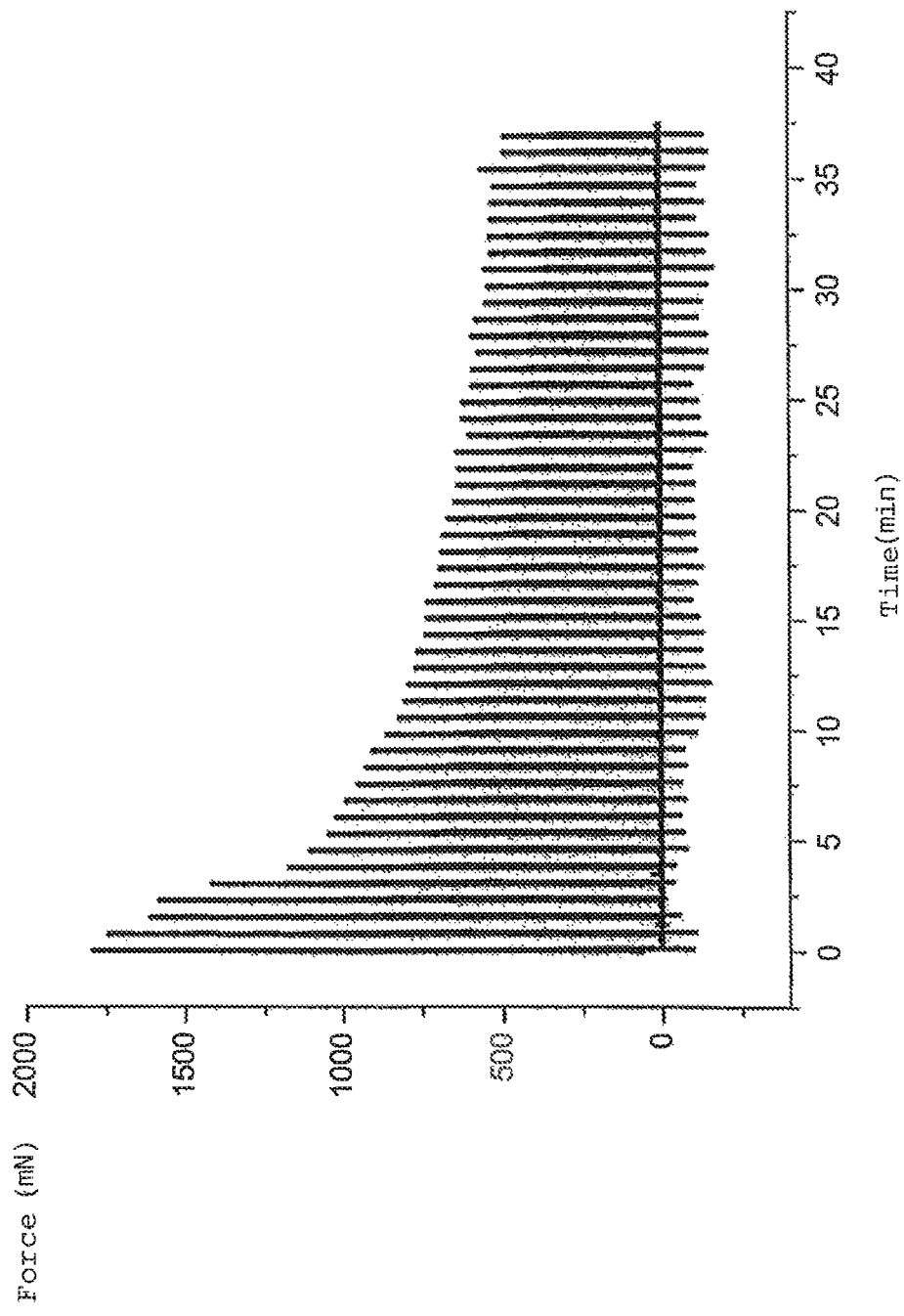
FIG. 2: is a graph, in which the gel strength and viscidity of a conventional composition based on thrombin and fibrinogen are plotted in dependence on the reaction time.

The result of the measurement is shown in the graph in FIG. 2. On comparison with FIGS. 1A to 1D it immediately becomes clear that the gel formation in the case of the fibrin glue has a completely different course from the medical glue according to the invention: the composition becomes solid more or less abruptly, i.e. the gel strength reaches its maximum value within a few seconds. The gel strength then decreases again (to less than half the initial value within 35 min). The gel exhibits significant syneresis.

A further advantage of the glue according to the invention is based on the two components gelatin and cross-linking agent being available in high and reproducible quality. As a result, the kinetics of the gel formation are also reproducible to a high degree with a given quantitative composition. In contrast, significant deviations in gel formation were observed in some instances in the examined fibrin glue, depending on the respective batch, which might be based, inter alia, on the human origin of some components that are subject to a natural fluctuation in quality.

Significant differences were also evident in the viscidity. The adhesion of the fibrin glue on the plastic surface of the plunger used is substantially constant in FIG. 2 during the measurement period of 35 min, while in the glues according to the invention from Example 1 an increase in adhesion resulting from the increase in gel strength can be observed.

However, with the exception of batch A, a noticeably higher adhesion is obtained than with the fibrin glue, which clearly shows a further advantage of the present invention. A very good adhesion can even be achieved with respect to a smooth plastic surface, as used in this test, e.g. over 200 mN/cm² in the case of batch C. Therefore, the medical glue according to the invention is not only suitable for gluing tissue, but also implants that have a smooth surface, for example.

The invention claimed is:

1. A method of producing and applying a medical glue to an area of application of a human or animal body, the medical glue forming a cross-linked gelatin gel in the area of application of the human or animal body, the method comprising:
   providing (A) a gelatin which has been partially cross-linked enzymatically by a transglutaminase and (B) a transglutaminase, both in separate chambers of a multi-chamber applicator; and
   applying said partially cross-linked gelatin and the transglutaminase simultaneously or consecutively to the area of application, resulting in formation of the medical glue,
   wherein said partially cross-linked gelatin and the transglutaminase are in the separate chambers until said partially-cross-linked gelatin and the transglutaminase are applied simultaneously or consecutively to the area of application, and wherein a 6.7% by weight (wt.) standard solution of said partially cross-linked gelatin in water at 60° C. has a viscosity of 7 mPa·s or more as a result of said partial cross-linking.

2. The method according to claim 1, wherein the gelatin is a fish gelatin.

3. The method according to claim 1, comprising providing said partially cross-linked gelatin in the form of an aqueous solution and providing the transglutaminase in a separate aqueous solution.

4. The method according to claim 3, comprising simultaneously applying the aqueous solution comprising said partially cross-linked gelatin and the aqueous solution comprising the transglutaminase by injection using the multi-chamber applicator.

5. The method according to claim 1, wherein providing said partially cross-linked gelatin and the transglutaminase in the separate chambers of a multi-chamber applicator comprises providing said partially cross-linked gelatin in the form of an aqueous solution and providing the transglutaminase in a solid form.

6. The method according to claim 1, wherein the gelatin concentration in the medical glue amounts to 5 to 20% by wt.

7. The method according to claim 1, wherein the cross-linked gelatin gel has a gel point that is reached 10 minutes or less after the start of a cross-linkage reaction, based on a predetermined temperature of the area of application.

8. The method according to claim 1, wherein the cross-linked gelatin gel has a gel strength of 100 g or more, as measured with a plunger with a diameter of 12.7 mm at a penetration depth of 4 mm.

9. The method according to claim 1, wherein the cross-linked gelatin gel has a gel strength and a gel point, wherein the gel strength of said cross-linked gelatin gel increases in the first 10 min after reaching the gel point at a rate of 5 to 200 mN/cm² min.

10. The method according to claim 1, wherein the cross-linked gelatin gel has an adhesion on a smooth plastic surface of 200 mN/cm² or more.

11. The method according to claim 1, wherein the medical glue comprises a viscosity-increasing polymer with a proportion of 1 to 10% by wt., based on the solid contents of the glue.

12. The method according to claim 11, wherein the viscosity increasing polymer is carboxymethylcellulose.

13. The method according to claim 1, wherein the medical glue comprises one or more therapeutic active substances.

14. The method according to claim 1, wherein the area of application comprises human or animal skin that is injured and/or burned.

15. The method according to claim 1, comprising fixing autologous or allogenic tissue in an area of application of the human or animal body, comprising applying the medical glue to the area of the tissue.

16. The method according to claim 1, comprising fixing an implant in an area of application of the human or animal body, comprising applying the medical glue to the implant.

* * * * *